United States Patent
Farhat et al.

(10) Patent No.: US 9,409,010 B2
(45) Date of Patent: Aug. 9, 2016

(54) ELECTRODE FIXING SLEEVE WITH STIFFENED FASTENING PORTION AND METHOD FOR PRODUCTION THEREOF

(71) Applicant: BIOTRONIK SE & Co. KG, Berlin (DE)

(72) Inventors: Chiheb Farhat, Berlin (DE); Siegfried Voigt, Berlin (DE); Ines Große, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 14/595,343

(22) Filed: Jan. 13, 2015

(65) Prior Publication Data

US 2015/0209574 A1     Jul. 30, 2015

Related U.S. Application Data

(60) Provisional application No. 61/932,804, filed on Jan. 29, 2014.

(51) Int. Cl.
*A61N 1/05* (2006.01)
*B29C 39/02* (2006.01)
*B29L 31/00* (2006.01)

(52) U.S. Cl.
CPC *A61N 1/05* (2013.01); *A61N 1/057* (2013.01); *B29C 39/026* (2013.01); *A61N 1/059* (2013.01); *A61N 1/0539* (2013.01); *A61N 1/0558* (2013.01); *A61N 2001/0582* (2013.01); *B29L 2031/753* (2013.01); *Y10T 29/49947* (2015.01)

(58) Field of Classification Search
None
See application file for complete search history.

(56) References Cited

U.S. PATENT DOCUMENTS

| | | |
|---|---|---|
| 2009/0125059 A1 | 5/2009 | Verzal et al. |
| 2010/0324569 A1 | 12/2010 | Helgesson |
| 2012/0071959 A1 | 3/2012 | Helgesson |
| 2012/0197367 A1 | 8/2012 | Olson et al. |

OTHER PUBLICATIONS

European Search Report and Notes to the European Search Report on European Patent Application No. EP 15 15 0321, dated Apr. 24, 2015 (7 pages).

*Primary Examiner* — Brian T Gedeon
(74) *Attorney, Agent, or Firm* — Buchanan Ingersoll & Rooney PC (57) ABSTRACT

An electrode fixing sleeve is provided for fixing an electrode to a tissue portion of a patient, and also provided is a method for production thereof. In order to avoid damaging the electrode as a result of the fastening thereof to the electrode fixing sleeve, the fastening portion is formed with a greater rigidity than an adjacent portion of the electrode fixing sleeve.

13 Claims, 6 Drawing Sheets

ELECTRODE FIXING SLEEVE WITH STIFFENED FASTENING PORTION AND METHOD FOR PRODUCTION THEREOF

CROSS-REFERENCE TO RELATED APPLICATIONS

This patent application claims the benefit of U.S. Provisional Patent Application No. 61/932,804, filed on Jan. 29, 2014, which is hereby incorporated by reference in its entirety.

TECHNICAL FIELD

The present invention relates to an electrode fixing sleeve for fixing an electrode to a tissue portion of a patient, comprising a fastening portion for fastening the electrode fixing sleeve to the electrode, wherein the electrode fixing sleeve forms a receiving tube for the electrode, said receiving tube extending in the longitudinal direction of said sleeve through the fastening portion, and can be compressed against a radial direction running perpendicular to the longitudinal direction. The present invention further relates to a method for producing an electrode fixing sleeve for fixing an electrode to a tissue portion of a patient, comprising a fastening portion for fastening the electrode fixing sleeve to the electrode, wherein the electrode fixing sleeve comprises a receiving tube for the electrode, said receiving tube extending in the longitudinal direction of said sleeve through the fastening portion, and comprising the fastening portion which can be compressed against a radial direction running perpendicular to the longitudinal direction.

BACKGROUND

Electrode fixing sleeves and methods for the production thereof are known in general. Electrode fixing sleeves are easily deformable, with the result that they can be inserted at least in part into vessels without damaging the vessels. With known electrode fixing sleeves, there is the problem, however, that the electrode guided through the electrode fixing sleeve may be damaged if an excessive pressure is exerted onto the electrode fixing sleeve by a fastening force for fastening the electrode fixing sleeve to the electrode. Protective sleeves which, when implanting the electrode fixing sleeve, are arranged between the electrode fixing sleeve and the electrode in order to protect the electrode against mechanical overload, hinder the insertion and fastening of the electrode fixing sleeve, with the result that a doctor inserting the electrode fixing sleeve has to expend greater effort.

The present invention is directed toward overcoming one or more of the above-mentioned problems.

SUMMARY

An object of the present invention is therefore to provide an electrode fixing sleeve and a method for the production thereof, wherein the electrode fixing sleeve can be easily implanted and the electrode is protected against damage.

For the electrode fixing sleeve mentioned in the introduction, at least this object is achieved in accordance with the present invention in that the fastening portion has a greater rigidity than an adjacent portion of the electrode fixing sleeve. For the method mentioned in the introduction, at least this object is achieved in that the fastening portion is formed with a greater rigidity than an adjacent portion of the electrode fixing sleeve.

Due to the greater rigidity of the fastening portion compared to the adjacent portion, for example, a guide portion which, for example, can be inserted into a vessel, local overloading of the electrode, as is caused, for example, by the use of ligature threads which, by means of constriction, attempt to reduce an inner diameter of the receiving tube and thus fasten the electrode fixing sleeve to the electrode, are reliably prevented. The stiffer fastening portion distributes the fastening forces and, in particular, prevents punctiform or linear overload. Since the electrode fixing sleeve outside the fastening portion may further have a greater flexibility than in the region of the fastening portion, the electrode fixing sleeve can be easily inserted as before into vessels of the patient, without hereby damaging the vessels.

A solution according to the present invention can be further improved by various embodiments that are each advantageous per se and can be combined arbitrarily with one another. These embodiments and the advantages associated therewith will be discussed hereinafter.

A stiffening element may thus be integrated into the fastening portion. In particular, the stiffening element may be connected captively to a wall material of the fastening portion. The electrode fixing sleeve may thus comprise the stiffening element, wherein the stiffening element is arranged in the fastening portion or is even fastened thereto and has a greater rigidity than the wall material of the electrode fixing sleeve. Here, the stiffening element may be an integral component of the electrode fixing sleeve. The stiffening element is held captively in the electrode fixing sleeve and is integrated there into, with the result that the stiffening element does not have to be handled separately when implanting the electrode fixing sleeve. The stiffening element also cannot shift when the electrode is inserted or passed through the receiving tube if the stiffening element is fastened non-displaceably or captively to the wall material. The electrode fixing sleeve is thus formed such that it can be handled integrally together with the stiffening element, with the result that the stiffening element does not have to be separately handled or secured when inserting the electrode.

In order to be able to fasten the electrode in the region of the fastening portion in the electrode fixing sleeve, the stiffening element may be deformable and, in particular, compressible against the radial direction. For example, fastening forces that can be applied by the ligature thread may deform or compress the stiffening element, with the result that the stiffening element can forward the fastening forces applied by the ligature thread to the electrode in a distributed manner. The electrode may therefore be held in a force-locked manner in the receiving tube. The stiffening element here distributes the fastening forces of the ligature thread, which, for example, are applied in a linear manner, such that local mechanical overloading of the electrode is prevented.

In order to ensure that the stiffening element is held non-displaceably by the wall material of the electrode fixing sleeve, in particular along the longitudinal direction, the stiffening element may be embedded into the wall material of the fastening portion, in particular in the radial direction. Since the stiffening element is embedded or sunk into the wall material, in particular in the radial direction, it is held non-displaceably by the wall material at least in and, where possible, also against the longitudinal direction, with the result that relative movements of the electrode along the longitudinal direction through the receiving tube cannot lead to a displacement of the stiffening element relative to the wall material and also along the longitudinal direction.

The stiffening element may border a receiving volume for the electrode, said receiving volume being delimited or defined by the receiving tube. The stiffening element may thus bear directly against the electrode and thus reliably mechanically contact and hold said electrode. In order to ensure that the electrode can slide easily through the receiving tube along the longitudinal direction, an inner face of the stiffening element may be in line with an inner face of the fastening portion, at least in the uncompressed state of the electrode fixing sleeve. The receiving tube may thus be delimited substantially without a step at the transition from wall material to stiffening element. A collision between the electrode and a protruding portion of the stiffening element or of the wall material is therefore reliably prevented, with the result that the electrode can be easily inserted into the receiving tube.

In accordance with a particularly advantageous embodiment, the stiffening element can be formed as a hollow coil, wherein the stiffening element winds around the receiving volume for the electrode and a central axis of the hollow coil is oriented parallel to the longitudinal direction. Due to the formation of the stiffening element as a hollow coil, the electrode, in the region of the fastening portion, is protected on all sides against overload, since it is surrounded in the region of the fastening portion by the hollow coil. Even if individual turns of the hollow coil do not bear against one another and, therefore, do not tightly surround the electrode, at least in the uncompressed state of the fastening portion, the hollow coil distributes fastening forces such that linear stresses are delivered to the electrode in a distributed manner.

If, in order to fasten the electrode fixing sleeve to the electrode, the fastening forces acting against the radial direction are exerted onto the fastening portion, an inner diameter of the hollow coil can thus be reduced. Specifically, the hollow coil can be deformable by means of the fastening forces, such that its inner diameter changes, in particular, uniformly along the longitudinal direction. The hollow coil is preferably resiliently deformable against the radial direction. If the electrode, for example, is to be removed again from the electrode fixing sleeve, it is thus sufficient to reduce the fastening forces and, for example, to loosen or to remove the ligature thread. A resilient restoring force of the hollow coil dilates the inner diameter thereof if the fastening forces are too low, with the result that the electrode can be easily removed through the receiving tube. Alternatively or additionally, the wall material can be resiliently deformable against the radial direction and can apply the restoring force or contribute thereto. For the at least partial transmission of the restoring force from the wall material to the stiffening element, the stiffening element adheres preferably to the wall material.

The hollow coil may comprise a wound stiffening sheet or may consist of such a sheet, wherein faces of the stiffening sheet running parallel to the longitudinal direction are larger than faces of the stiffening sheet running transversely to the longitudinal direction. The stiffening sheet may thus be formed in a strip-shaped manner, wherein the stiffening sheet winds around the central axis of the hollow coil. The ratio of the faces of the stiffening sheet ensures that the stiffening sheet takes up less space in the radial direction. Furthermore, the hollow coil can bear against the electrode over the greatest area possible due to the large faces running parallel to the longitudinal direction, with the result that the fastening forces can be distributed optimally. The hollow coil can be formed with different cross-sections, for example, rectangular or oval.

A distance between adjacent turns of the hollow coil, said distance being measured parallel to the longitudinal direction, is preferably smaller than a width of the stiffening sheet measured parallel to the longitudinal direction. Since the turns do not bear against one another, easy deformation of the hollow spring along the radial direction is ensured. If the turns were to bear against one another, the deformability of the stiffening element formed as a hollow coil would be considerably impaired. The small distance compared to width ensures that the fastening forces do not overload the electrode past the stiffening sheet.

In order to be able to protect the electrode against overload transverse to the longitudinal direction on all sides, the hollow coil may have at least one turn. If the hollow coil has less than one turn, at least a portion of the electrode in a circumferential direction of the electrode fixing sleeve can thus be reached by punctiform or linear stresses caused by fastening forces, for example, caused by the ligature thread, and may thus be mechanically overloaded.

The hollow coil may also have more than one turn so that a larger portion of the receiving tube can be surrounded by the hollow coil along the longitudinal direction. The electrode can thus be protected against overload over a large area along the longitudinal direction, and the fastening forces can be distributed over a larger area.

The undeformed hollow coil preferably has a whole number of turns. For example, the hollow coil may have 2, 3, 4, 5, 7 or up to 10 or even more turns. Along the longitudinal direction, fastening forces occurring in the case of a hollow coil having a whole number of turns can be distributed more uniformly, in particular, at ends of the hollow coil arranged in and against the longitudinal direction, compared to a hollow coil having an unwhole (i.e., fractional) number of turns.

The hollow coil is formed, for example, as a left-hand or as a right-hand helix, which winds with constant pitch around the receiving tube. The pitch of the hollow coil may be low in order to be able to arrange as many turns as possible in the fastening portion. In particular, an angle between the longitudinal direction and the faces of the stiffening sheet running transversely to the longitudinal direction may be greater than 45°, and, for example, may be 60°, 70°, 80° or even 85°.

It is not only a mechanical overload of the electrode that is reliably prevented, however, by the use of the stiffening element in the form of a hollow coil. In particular, the faces running transversely to the longitudinal direction may increase an inner sealing section of the electrode fixing sleeve, such that fluids penetrating the electrode fixing sleeve cannot pass through the electrode fixing sleeve or can only pass through the electrode fixing sleeve in a delayed manner.

Alternatively to the embodiment of the stiffening element in the form of a hollow coil, the stiffening element may also be formed as a stiffening sleeve cut along the longitudinal direction and openable transversely to the longitudinal direction. In the closed state of the stiffening sleeve, it can be formed, for example, in a cylindrical manner, wherein a vertical direction of the cylinder extends parallel to the longitudinal direction. To open the stiffening sleeve, it may comprise two partial shells that are interconnected so as to be movable relative to one another. For example, the partial shells may be interconnected via a hinge. In order to prevent undesirable opening of the stiffening sleeve, said sleeve may comprise a latching device which can hold the partial shells in a closed position. To open the latched partial shells, a latching member of one of the partial shells can be resiliently pressed out from a latched position. In so doing, the stiffening sleeve itself may produce opening forces which move the partial shells in order to open the stiffening sleeve as soon as the latched connection between the partial shells is released. Alternatively or additionally, the wall material of the electrode fixing sleeve can be resiliently deformed when the stiffening sleeve is in the closed state, such that the wall material opens the receiving sleeve as soon as the latched connection between the partial shells is released.

For example, the latching members of the partial shells may be formed differently. In particular, the latching member of one of the partial shells may be arranged on an inner face and the latching member of the other of the partial shells may be arranged on an outer face of the respective partial shell.

In accordance with a further possible embodiment, the stiffening element may be formed as a thick-walled stiffening or receiving cylinder, of which the outer diameter may be much larger than other portions of the electrode fixing sleeve and, in particular, than an outer diameter of the guide portion of the electrode fixing sleeve. So that the thick-walled receiving cylinder can be inserted into the electrode fixing sleeve, it may form a receiving container, wherein two partial shells of the receiving container can be fitted onto the receiving cylinder parallel to the longitudinal direction.

A further alternative possibility for forming the stiffening element is that of forming the stiffening element in a cylindrical manner. The cylindrical stiffening element however is often deformable in the radial direction only with difficulty or is not deformable in the radial direction with the fastening forces present. So that the electrode can be fastened in the electrode fixing sleeve, the electrode fixing sleeve may have a fixing element that can be inserted in addition to the electrode into the cylindrical stiffening element and presses the electrode in the stiffening element. The fixing element can be inserted into the cylindrical stiffening element along the longitudinal direction, for example. Alternatively, the fixing element can be inserted into the stiffening element against the radial direction.

In addition, instead of the use of ligature threads, a clamping arrangement can be provided which does not apply linear or punctiform fastening forces, but applies fastening forces over a large area. The clamping arrangement preferably comprises a substantially cylindrical clamping portion which is cut along the longitudinal direction and is resiliently deformable transversely to the longitudinal direction. To apply the fastening forces, the clamping arrangement may comprise two force take-up portions which protrude in the radial direction from sides of the force take-up portion arranged opposite one another along the circumferential direction. For example, the force take-up portions may comprise openings for receiving a screw, wherein the screw introduces the fastening force into the force take-up portions, from where it is guided through the clamping portion to the force take-up portion of the electrode fixing sleeve or directly to the electrode.

The stiffening element can be produced from various materials, for example, from a metal, polymer or thermoplastic. The surface of the stiffening element may additionally be treated using various surface methods, for example, etching, radiation, milling or turning, in order to thus achieve improved adhesion to the electrode. The electrode fixing sleeve may be cast, for example, from a resin, a polymer, an elastomer or from a thermoplastic, wherein the wall material is cast around the stiffening element at least in part.

The present invention will be explained in greater detail hereinafter on the basis of exemplary embodiments with reference to the drawings. The individual features of the embodiments can be combined with one another arbitrarily.

Further features, aspects, objects, advantages, and possible applications of the present invention will become apparent from a study of the exemplary embodiments and examples described below, in combination with the Figures, and the appended claims.

DETAILED DESCRIPTION

The design and function of an electrode fixing sleeve according to the present invention will first be described with reference to the exemplary embodiment in FIG. 1.

Figure 1:
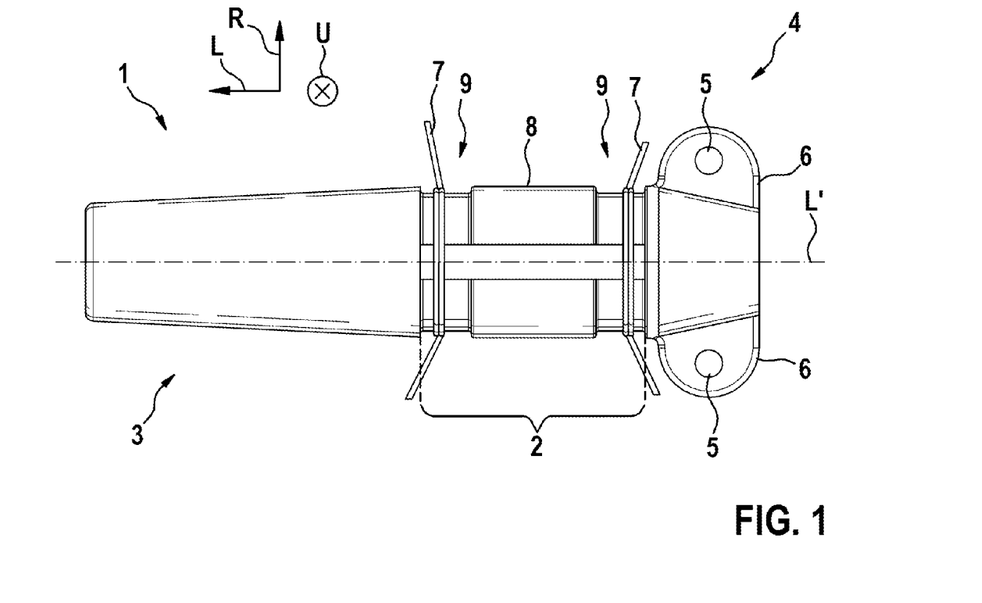
FIG. 1 shows a first exemplary embodiment of an electrode fixing sleeve in a side view.

FIG. 1 shows an electrode fixing sleeve 1 schematically in a side view. A receiving tube (not visible in the side view in FIG. 1) for receiving an electrode extends through the electrode fixing sleeve 1 along the longitudinal direction L thereof. The receiving tube defines a preferably cylindrical receiving volume for the electrode, wherein the receiving volume extends along a longitudinal axis L' of the electrode fixing sleeve 1.

The electrode fixing sleeve 1 is formed with a fastening portion 2, which is deformable toward the longitudinal axis L' against a radial direction R running transversely to the longitudinal direction L. If the fastening portion 2 is deformed in the direction of the longitudinal axis L', an inner diameter of the receiving tube thus reduces. A force-locked connection is thus produced between the electrode fixing sleeve 1 and the electrode inserted into the receiving tube.

The electrode fixing sleeve 1 may have a guide portion 3 in the longitudinal direction L, through which the receiving tube likewise extends and which guides the electrode. In the implanted state of the electrode fixing sleeve 1, the guide portion 3 may protrude at least in part into a vessel through which the electrode may extend as far as an organ, for example, the heart, of a patient. The guide portion 3 is thus preferably formed resiliently such that it does not damage the vessel unnecessarily.

Before the fastening portion 2 in the longitudinal direction L, the electrode fixing sleeve 1 may comprise a fixing portion 4, which is designed to fix the electrode fixing sleeve 1 to a tissue portion of the patient. The fixing portion 4 may comprise at least one fixing opening 5, through which the electrode fixing sleeve 1 can be sewn to the tissue portion. The fixing opening 5 extends, for example, perpendicularly to the longitudinal direction L through a fixing tab 6 extending away from the longitudinal axis L'. In particular, the fixing portion 4 comprises two fixing openings 5, which are arranged symmetrically with respect to the longitudinal axis L'. If two fixing openings 5 are provided, two fixing tabs 6 may thus also be formed, wherein each one of the fixing openings 5 extends through a respective one of the fixing tabs 6, and wherein the two fixing tabs 6 extend away from the longitudinal axis L' and away from one another.

In order to produce the force-locked connection between the fastening portion 2 and the electrode, fastening forces acting against the radial direction R are exerted onto the fastening portion 2. The fastening forces may be produced, for example, by a ligature thread 7, which is to be tied around the fastening portion 2. Since the ligature thread 7 causes linear fastening forces, which are transmitted to the electrode through a wall material 8 of the fastening portion 2, there is a risk of damaging the electrode if a stress produced by the linear fastening forces is excessive. In the exemplary embodiment shown in FIG. 1, two ligature threads are used to generate the fastening forces. The wall material 8 of the fastening portion 2 preferably corresponds, however, to the wall material 8 of the guide portion 3. Since the guide portion 3 is soft in order to avoid unnecessarily damaging the vessel, the wall material 8 in the region of the fastening portion 2 of known electrode fixing sleeves 1 is likewise soft and is therefore unable to distribute the fastening forces over a large area in order to prevent damage to the electrode. The fastening portion 2 of the electrode fixing sleeve 1 according to the present invention consequently preferably has a greater rigidity than the guide portion 3 and/or the fixing portion 4.

A fastening groove 9, which opens away from the longitudinal axis L' and is arranged in the region of the fastening portion 2, may extend along the circumferential direction U of the electrode fixing sleeve 1 running transversely to the longitudinal direction L and the radial direction R. The fastening groove 9 prevents the ligature thread 7 from shifting parallel to the longitudinal axis L', which facilitates a fastening of the electrode fixing sleeve 1 to the electrode. In particular, the fastening portion 2 may comprise two fastening grooves 9, which are distanced from one another in the longitudinal direction L. The fastening grooves 9 may form a front or a rear end of the fastening portion 2 in the longitudinal direction L. In addition to the holding function of the fastening groove 9, a thickness of the wall material 8 is reduced by the fastening groove 9, with the result that the fastening forces can be transmitted to the electrode more easily through the electrode fixing sleeve 1.

Figure 2:
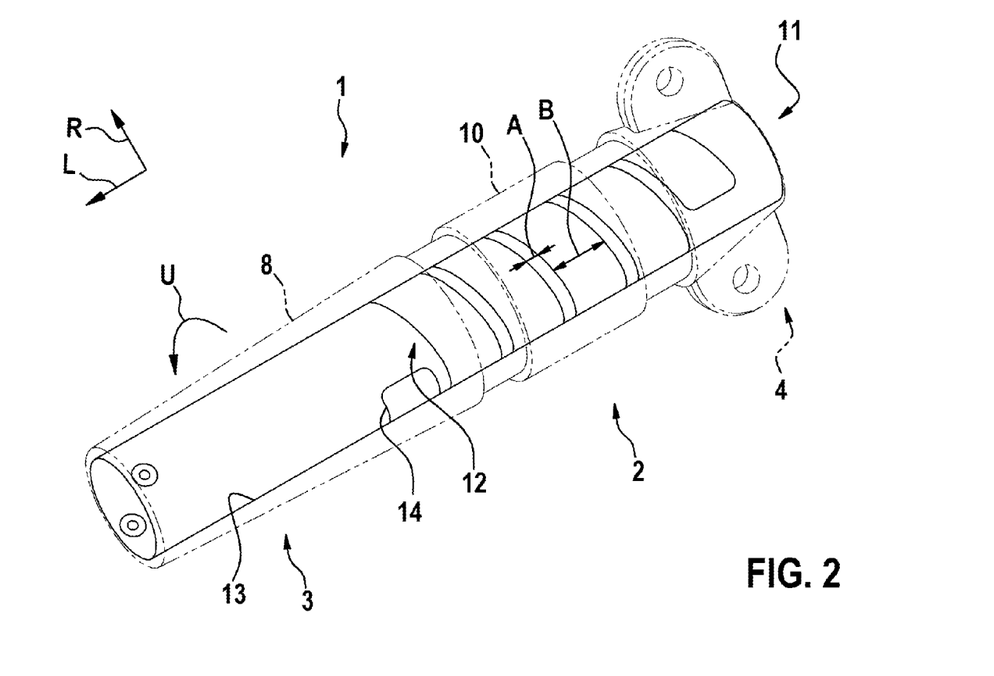
FIG. 2 shows a perspective view of an electrode fixing sleeve of a further exemplary embodiment of FIG. 1 in a transparent view.

FIG. 2 shows a further exemplary embodiment of the electrode fixing sleeve 1 according to the present invention schematically in a transparent perspective illustration Like reference signs are used for elements that correspond in terms of function and/or design to the elements in the prior exemplary embodiment. For the sake of brevity, merely the differences from the prior exemplary embodiment will be discussed.

The electrode fixing sleeve 1 is shown in FIG. 2 with a stiffening element 10 that is arranged in the region of the fastening portion 2. The stiffening element 10 increases the rigidity of the fastening portion 2 without the need for the wall material 8 of the electrode fixing sleeve 1 to differ in the region of the fastening portion 2 from the wall material 8 of the rest of the electrode fixing sleeve 1. Without the stiffening element 10, the electrode fixing sleeve 1 would have to be formed in the region of the fastening portion 2 with a wall material 8 that is different from the wall material in the region of the guide portion 3 and/or of the fixing portion 4. Alternatively, the wall thickness of the electrode fixing sleeve 1 in the region of the fastening portion 2 could differ from the wall thickness of the guide portion 3 and/or from the wall thickness of the fixing portion 4 and, in particular, could be greater in order to be able to better distribute prevailing fastening forces. A provision of the stiffening element 10, however, facilitates the fabrication of the electrode fixing sleeve 1 and prevents the electrode fixing sleeve 1 from being unnecessarily thickened in the region of the fastening portion 2. As illustrated in the exemplary embodiment in FIG. 2, the stiffening element 10 may extend over the fastening portion 2 in and/or against the longitudinal direction L in order to also be able to effectively distribute fastening forces acting on an end or a starting point of the fastening portion 2.

The stiffening element 10 is deformable against the radial direction R, with the result that it can transmit the fastening forces to the electrode. The stiffening element 10 is preferably resiliently deformable against the radial direction R, with the result that, with a reduction of the fastening forces, the deformation of the stiffening element 10 decreases and the stiffening element 10 can return at least in part into its undeformed state. A removal or a subsequent displacement of the electrode in/or against the longitudinal direction L is thus simplified. The receiving tube 11 extending through the electrode fixing sleeve 1 can be seen in FIG. 2. The receiving tube 11 extends in the longitudinal direction L through the fastening portion 2 and through the guide portion 3 and the fixing portion 4. It opens in and against the longitudinal direction L, with the result that the electrode can be slid though the receiving tube 11. The receiving tube 11 defines a receiving volume, into which the electrode can be inserted at least in part.

If the electrode is slid into or through the receiving tube 11 in or against the longitudinal direction L, there is thus the risk that the stiffening element 10 will be displaced parallel to the longitudinal direction L. If the stiffening element 10 is slid out too far from the fastening portion 2, it may therefore no longer sufficiently distribute the prevailing fastening forces, whereby the risk of damaging the electrode would be increased. In order to prevent an unwanted displacement of the stiffening element 10, the stiffening element 10 is preferably sunk into the wall material 8. For example, the wall material 8 may be cast around the stiffening element 10 at least in portions and the stiffening element may even adhere to the wall material.

The stiffening element 10 is thus fastened captively to the wall material 8 and forms an integral part of the electrode fixing sleeve 1. The electrode fixing sleeve 1 with the stiffening element 10 can consequently be handled in one piece, with the result that the stiffening element 10 does not have to be handled separately when the electrode fixing sleeve 1 is to be implanted.

The stiffening element 10 may border the receiving volume for the electrode, said receiving volume being defined by the receiving tube 11. The stiffening element 10 may therefore bear against the electrode when the electrode is fastened to the electrode fixing sleeve 1. A stiffening element 10 bearing against the electrode generates a defined contact between the electrode fixing sleeve 1 and the electrode, whereby the reliability of the fastening of the electrode fixing sleeve 1 to the electrode is improved.

An inner face 12 of the stiffening element 10 is preferably in line with an inner face 13 of the wall material 8, at least in the region of the fastening portion 2 and preferably also in the region of the guide portion 3 and/or the fixing portion 4, with the result that the receiving tube 11 can extend continuously through the electrode fixing sleeve 1, at least in the region of the fastening portion 2. Specifically, the electrode may become caught on steps or edges as it is inserted into the receiving tube 11, whereby insertion of the electrode would be impaired.

In the exemplary embodiment in FIG. 2, the stiffening element 10 is formed by way of example as a hollow coil, of which the central axis is in line with the longitudinal axis L'. The stiffening element 10 in the form of a hollow coil winds around the receiving tube 11 and has five turns in accordance with the illustrated exemplary embodiment.

The stiffening element 10 in the form of a hollow coil is formed by a wound stiffening sheet, of which the inner face 12 running parallel to the longitudinal direction L is larger than its face 14 running transversely to the longitudinal direction L. The stiffening element 10 in the form of a hollow coil may have a rectangular cross section along the longitudinal direction L.

A distance A between adjacent turns of the stiffening element 10 formed as a hollow coil, said distance extending parallel to the longitudinal direction L, is preferably smaller than a width B of the stiffening sheet to be measured parallel to the longitudinal direction L. Due to the distance A, a uniform deformability of the stiffening element 10 formed as a hollow coil is ensured when the fastening forces act on the electrode fixing sleeve 1.

If the electrode fixing sleeve 1 is deformed against the radial direction R toward the longitudinal axis L' as a result of the fastening forces, an inner diameter of the stiffening element 10 formed as a hollow coil thus reduces uniformly along the longitudinal direction L, with the result that punctiform or linear stressing of the electrode are avoided.

Figure 3:
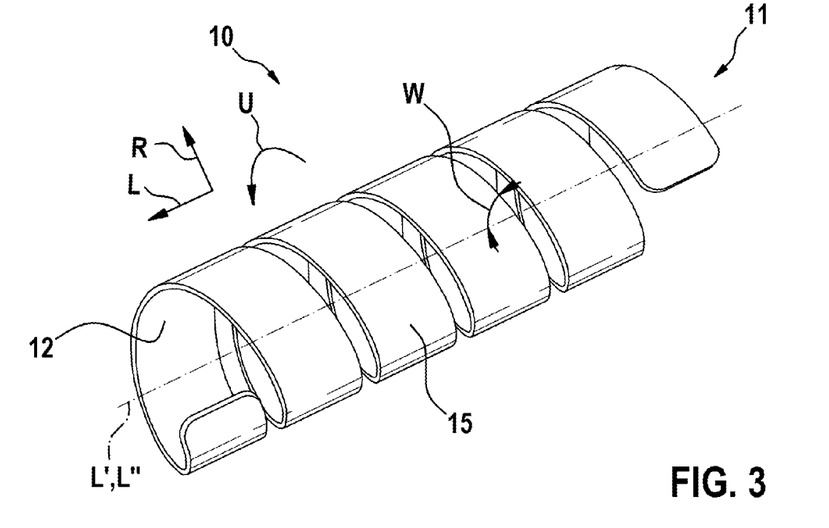
FIG. 3 shows a perspective illustration of a stiffening element of the electrode fixing sleeve of the exemplary embodiment in FIG. 2.

FIG. 3 schematically shows the stiffening element 10, formed as a hollow coil, of the exemplary embodiment in FIG. 2.

A central longitudinal axis L" of the stiffening element 10 formed as a hollow coil is in line with the longitudinal axis L' of the receiving tube 11. The stiffening element 10 formed as a hollow coil winds around the longitudinal axis L'. In order to be able to ensure the tightest possible contact between the stiffening element 10 formed as a hollow coil and the electrode, a pitch of the turns of the stiffening element 10 formed as a hollow coil is dimensioned such that an angle W between the longitudinal axis L" and the individual turns is as large as possible. In particular, the angle W is between 45° and 90° and for example is 60°, 70°, 80° or even 85°.

It can be clearly seen in the exemplary embodiment in FIG. 3 that the inner face 12 delimits the receiving tube 11 in the radial direction R, such that the receiving tube 11 may have the form of a straight cylinder at least in the region of the stiffening element 10 formed as a hollow coil. The inner faces 12 of the turns of the stiffening element 10 are in line here with the other turns, as are the outer faces 15 of the turns, these faces, in particular, running parallel to the longitudinal axis L", with the result that the outer face 15 and the inner face 12 of the stiffening element 10 in the form of a hollow coil follow a cylindrical form. A uniform deformation of the electrode fixing sleeve 1 in the region of the fastening portion 2 thus leads to a uniform transfer of the fastening forces to the electrode.

Figure 4:
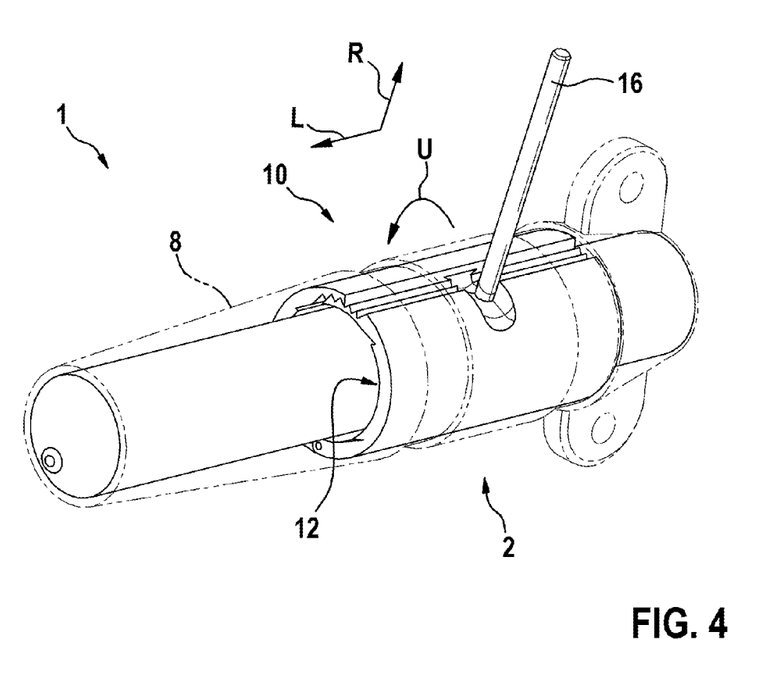
FIG. 4 shows a further exemplary embodiment of the electrode fixing sleeve in a transparent view.

FIG. 4 shows a further exemplary embodiment of the electrode fixing sleeve 1 according to the present invention schematically illustrated in a transparent perspective view. The same reference signs are used for elements that correspond in terms of function and/or design to the elements in the prior exemplary embodiments. For the sake of brevity, only the differences from the prior exemplary embodiments will be discussed.

The stiffening element 10 of the exemplary embodiment in FIG. 4 is formed as a stiffening sleeve which has partial shells that can be pivoted relative to one another in or against the circumferential direction U. FIG. 4 further shows an opening pin 16 for opening the stiffening sleeve. The stiffening element 10 formed as a stiffening sleeve is arranged in the fastening portion 2, similarly to the stiffening element 10 of the exemplary embodiment in FIGS. 2 and 3, and may protrude into the guide portion 3 and/or the fixing portion 4 in and against the longitudinal direction L. Wall material 8 may be provided on an inner face 12 of the stiffening element 10 in order to prevent direct contact between a portion of the stiffening element 10 and the electrode. In particular, the electrode can thus be reliably prevented from being pinched when the partial shells are closed.

Figure 5:
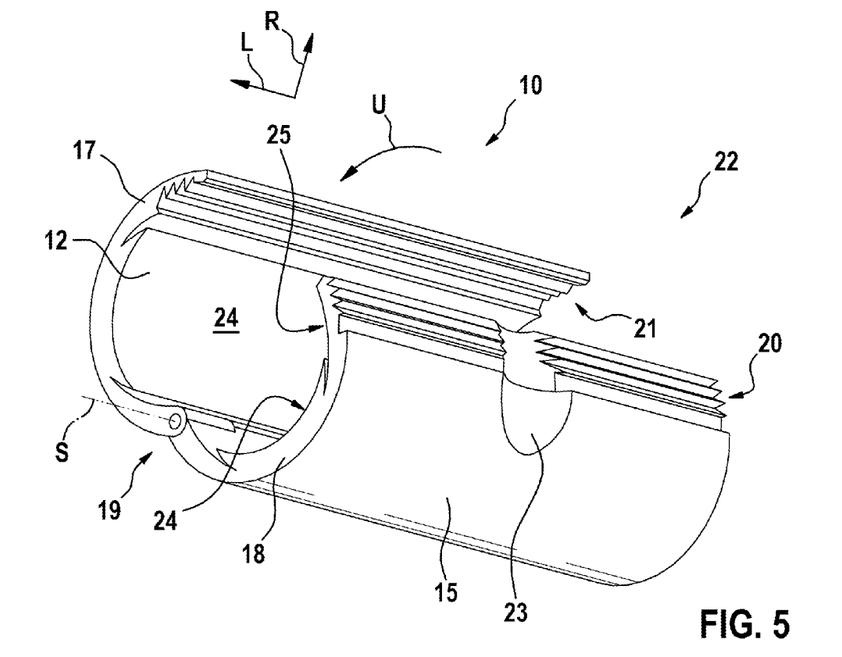
FIG. 5 shows a perspective view of a stiffening element of the exemplary embodiment illustrated in FIG. 4 of the electrode fixing sleeve.

Further details concerning the reinforcement element 10 formed as a stiffening sleeve are illustrated in FIG. 5, which shows the stiffening element 10 of the exemplary embodiment formed as a stiffening sleeve schematically in an open perspective view.

The stiffening element 10 of the exemplary embodiment in FIG. 5 is formed with two partial shells 17, 18, which can be pivoted relative to one another about a common pivot axis S in or against the circumferential direction U. The pivot axis S preferably runs parallel to and at a distance from the longitudinal axis L" (see e.g., FIG. 3).

In order to be pivotally interconnected, the partial shells 17, 18 form a hinge 19 which defines the position of the pivot axis S. End portions of the partial shells 17, 18 arranged opposite the hinge 19 in or against the circumferential direction U are provided with latching members 20, 21, wherein the latching members 20, 21 form a latching device 22 of the stiffening sleeve. The latching device 22 fastens the partial shells 17, 18 to one another in a closed state, with the result that the stiffening sleeve cannot be opened unintentionally.

The latching member 20 of the partial shell 18 is arranged, for example, on the outer face 15 of the stiffening element 10, and the latching member 21 is arranged, for example, on the inner face 12 of the partial shell 17. When the stiffening element 10 is closed, the latching members 20, 21 point toward one another and bear against one another. For example, the latching members 20, 21 may each comprise latching elements or mating latching elements, for example, in the form of latching teeth or latching bars, which enable the stiffening element 10 to be closed by pivoting the partial shells 17, 18 parallel to the circumferential direction U and toward one another. When the stiffening element 10 is closed, the partial shells 17, 18 are reliably prevented by the latching device 22 from pivoting about the pivot axis S away from one another.

To release the latched connection of the partial shells 17, 18 to one another, the partial shell 18, in particular, can be pressed against the radial direction R and in the direction of the longitudinal axis L' of the electrode fixing sleeve 1. If the latching members 20, 21 comprise latching teeth or latching bars, these are thus engaged with one another when the stiffening element 10 is closed. By displacing the latching member 20 of the partial shell 18 against the radial direction R, the latching elements of the latching member 20 are moved out from the engagement with the mating latching elements of the latching member 21, with the result that the latched connection is released and the stiffening element 10 can be opened. To deform the partial shell 18, the opening pin 16 can be pressed against the partial shell 18, against the radial direction.

In order to prevent the opening pin 16 from slipping from the partial shell 18, the stiffening element 10 may have a holding cavity 23 for the opening pin 16 in the region of the latching member 20, said cavity 23 curving into the stiffening element 10 against the radial direction R. The holding cavity 23 secures the opening pin 16 from slipping parallel to the longitudinal direction L or against the circumferential direction U. An opening for the opening pin 16, making the holding cavity 23 accessible against the radial direction R, can be formed in the wall material 8 of the electrode fixing sleeve 1. So that the opening pin 16 can reliably deform the partial shell 18, without slipping therefrom, even when the stiffening element 10 is only partly closed, the holding cavity 23 may extend in the circumferential direction U until between the latching elements of the latching member 20.

In the region of the hinge 19 and of the latching members 20, 21, there is a risk of damaging the electrode when closing the stiffening element 10 formed as a stiffening sleeve. In order to be able to keep the electrode at a distance from the hinge 19 and the latching device 22, at least one of the partial shells, 17, 18 preferably comprises a holding portion 24, which is arranged between the latching member 20, 21 and the hinge 19 in the circumferential direction U and which protrudes beyond the hinge S or the latching device 22 against the radial direction R and along the respective partial shell 17, 18. The electrode consequently bears against the fixing sleeve only in the region of the at least one holding portion 24. The holding portion 24 may border the receiving volume and may therefore directly contact the electrode. In particular, the hinge 19 and an inner face 25 of the latching member 20 pointing against the latching direction R toward the hinge 19 may be separated from the receiving tube 11 by wall material 8, with the result that they cannot directly contact the electrode.

Figure 6:
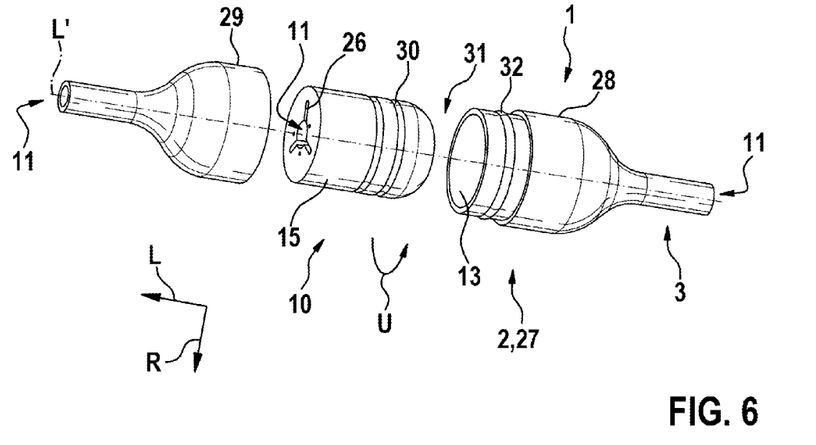
FIG. 6 shows a further exemplary embodiment of a stiffening element in a perspective view.

FIG. 6 shows a further exemplary embodiment of a stiffening element 10 for an electrode fixing sleeve 1. The same reference signs are used for elements that correspond in terms of function and/or design to the elements of the prior exemplary embodiments. For the sake of brevity, only the differences from the exemplary embodiments in the prior figures will be discussed.

The stiffening element 10 of the exemplary embodiment in FIG. 6 is formed as a stiffening cylinder. The receiving tube 11 extends through the stiffening cylinder along the longitudinal axis L', wherein an inner diameter of the receiving tube 11 is smaller than a maximum wall thickness of the thick-walled stiffening cylinder in the radial direction R. In order to be able to clamp the electrode in the stiffening cylinder and for this purpose to compress the stiffening cylinder against the radial direction R, the stiffening cylinder comprises at least one weakening groove 26, which extends parallel to the longitudinal axis L and opens against the radial direction R toward the receiving tube 11. The weakening groove 26 ends in the radial direction R before it reaches the outer face 15. Since an outer diameter transverse to the longitudinal axis L' of the stiffening element 10 formed as a thick-walled stiffening cylinder is much larger than an outer diameter of the guide portion 3, the electrode fixing sleeve 1 is formed with a receiving container 27 that forms the fastening portion 2. The receiving container 27 comprises two partial shells 28, 29, of which the inner diameter transverse to the longitudinal axis L' is larger than the inner diameter of the receiving tube 11, with the result that the stiffening element 10 formed as a thick-walled receiving cylinder can be arranged in the receiving container 27.

The stiffening element 10 can be inserted into the partial shell 28. In order to fix the stiffening element 10 in the partial shell 28 parallel to the longitudinal direction L, the stiffening element 10 on its outer face 15 has at least one latching element, for example, a latching groove 30 extending around the stiffening element 10 in the circumferential direction U. A mating latching element for the latching element of the stiffening element 10 is arranged on the inner face 13 of the partial shell 28, wherein the mating latching element can be formed, for example, as a latching protrusion or a latching bead extending against the radial direction R into the receiving container 27 and around the longitudinal axis L' in the circumferential direction U.

In order to be able to insert the stiffening element 10 of the exemplary embodiment in FIG. 6 easily into the partial shell 28, an end 31 formed in the longitudinal direction L is rounded.

If the stiffening element 10 is arranged in an assembled position in the partial shell 28, the stiffening element 10 and the partial shell 28 may thus border on a common plane in the longitudinal direction L.

The partial shell 29 can be fitted at least in portions onto the partial shell 28 in the longitudinal direction L. It may also be possible to fasten the partial shells 28, 29 to one another likewise via latching elements. For example, the partial shell 28 comprises a receiving bead 32 protruding away from the longitudinal axis L and extending around the longitudinal axis L' in the circumferential direction U, and the partial shell 29 comprises a complementary latching element arranged on its inner face.

Figure 7:
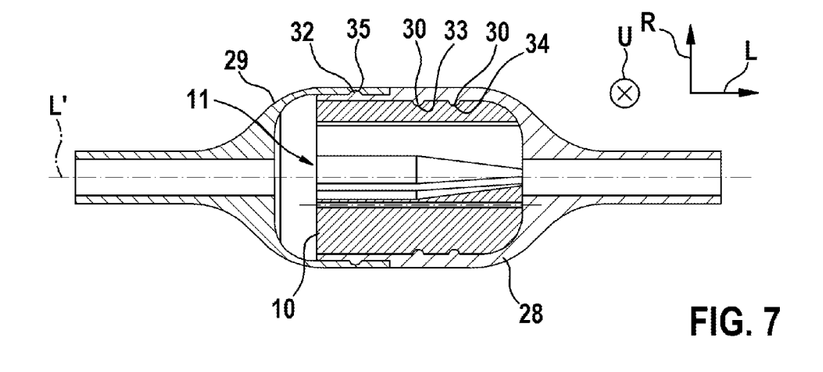
FIG. 7 shows a sectional illustration of an electrode fixing sleeve with a stiffening element according to the exemplary embodiment in FIG. 6.

FIG. 7 shows the exemplary embodiment in FIG. 6 schematically in a sectional view, wherein the plane of section runs along the longitudinal axis L'. The stiffening element 10 of the exemplary embodiment in FIG. 7 is provided with two latching grooves 30, which are distanced from one another along the longitudinal direction L. The partial shell 28 accordingly has two latching beads 33, 34 protruding toward the longitudinal axis L', which, when the stiffening element 10 is assembled, engage in the latching grooves 30 and thus prevent an unintentional displacement of the stiffening element 10 parallel to the longitudinal direction L and relative to the partial shell 28. The partial shells 28, 29 are likewise secured via a latched connection against unwanted relative movements along the longitudinal direction L. The latched connection is ensured here too by a latching groove 32 and a latching bead 35.

The stiffening element 10 is arranged at a distance from the partial shell 29 parallel to the longitudinal direction L and is fastened to the partial shell 28. Due to the distance between the stiffening element 10 and the partial shell 29, an over determinacy of the positions of the partial shells 28, 29 is prevented by the stiffening element 10, with the result that the partial shells 28, 29 can be securely fastened to one another by latching.

The receiving tube 11 may taper at least in portions in the longitudinal direction L within the stiffening element 10 in order to be able to easily guide the electrode. In particular, if the electrode is to be inserted into the receiving tube 11 in the longitudinal direction L, the electrode can be easily positioned by the tapering receiving tube 11, since the receiving tube 11 forms a funnel.

Figure 8:
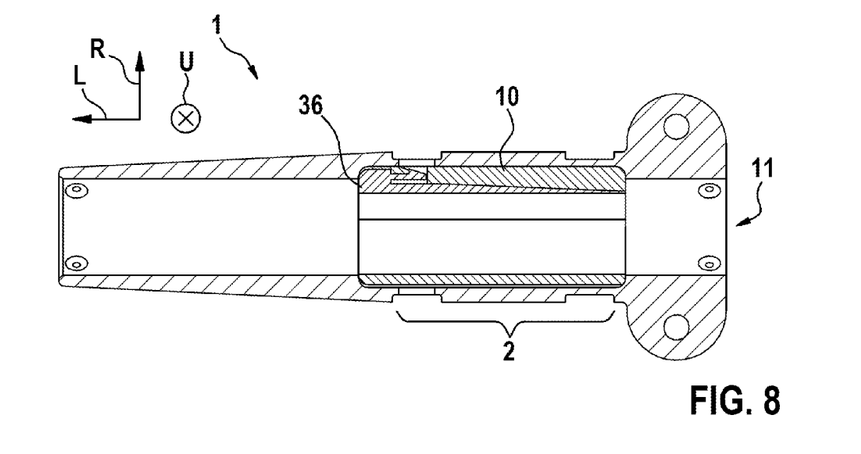
FIG. 8 shows a further exemplary embodiment of an electrode fixing sleeve in a sectional illustration.

FIG. 8 shows a further exemplary embodiment of the electrode fixing sleeve 1 according to the present invention schematically in a sectional illustration along the longitudinal axis L'. The same reference signs are used for elements that correspond in terms of function and/or design to the elements of the prior exemplary embodiments. For the sake of brevity, only the differences from the prior exemplary embodiments will be discussed.

The electrode fixing sleeve 1 is provided with a cylindrical stiffening element 10. The stiffening element 10 is formed as a hollow cylinder and may be substantially non-deformable by prevailing fastening forces, at least against the radial direction R. In the exemplary embodiment shown in FIG. 8 too, the receiving tube 11 extends through the electrode fixing sleeve 1 and the stiffening element 10.

In order to be able to fasten the electrode in the electrode fixing sleeve 1, the electrode fixing sleeve 1 has a clamping wedge 36, which, for example, can be inserted into the cylindrical stiffening element 10 against the longitudinal direction L.

Figure 9:
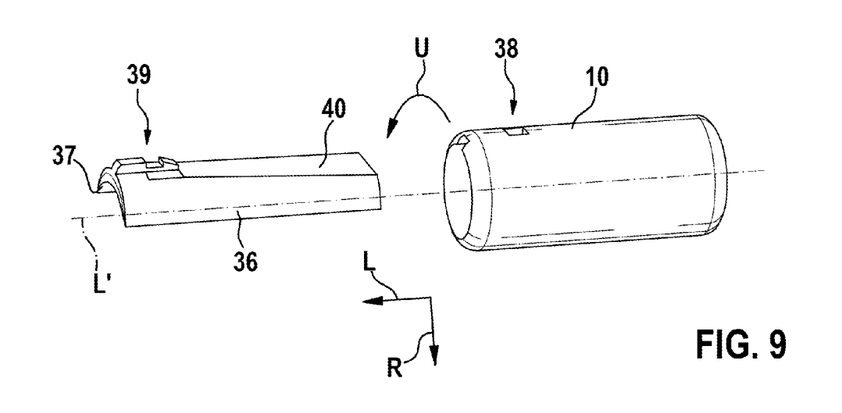
FIG. 9 shows a stiffening element in a perspective view according to the exemplary embodiment in FIG. 8.

Details concerning the stiffening element 10 and the clamping wedge 36 can be better seen in FIG. 9, which shows merely the cylindrical stiffening element 10 and the clamping wedge 36 schematically in a perspective view.

An inner face 37 of the clamping wedge 36 is formed in a substantially arcuate manner extending parallel to the circumferential direction U and bears against the receiving volume of the receiving tube 11 when the clamping wedge 36 is inserted into the cylindrical stiffening element 10 against the longitudinal direction L.

In order to be able to fix the clamping wedge 36 in the cylindrical stiffening element 10, the stiffening element 10 may comprise a latching element 38 and the clamping wedge 36 may comprise a mating latching element 39, wherein the mating latching element 39 is preferably provided on an outer face of the clamping wedge 36 arranged after the inner face 37 in the radial direction R. A clamping bevel 40 running at an incline with respect to the longitudinal axis L' and, in particular, away from the mating latching element 39 and, in so doing approaching the longitudinal axis L, may be provided against the longitudinal direction L and presses the clamping wedge 36 against the radial direction R toward the longitudinal axis L' during insertion into the cylindrical stiffening element 10, and thus reduces the inner diameter of the receiving tube 11 and thus presses against the electrode over a large area.

Figures 10, 11:
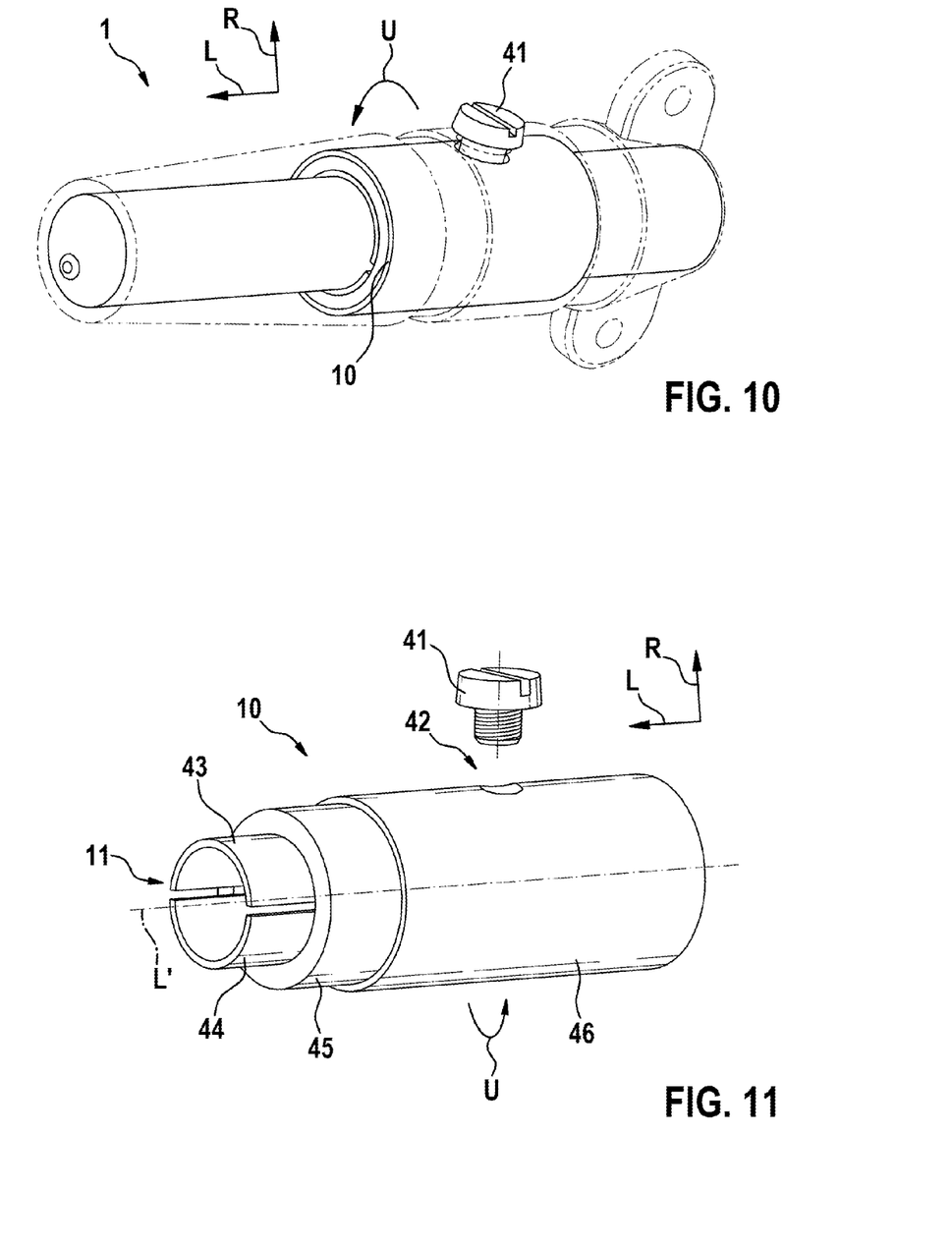
FIG. 10 shows a further exemplary embodiment of an electrode fixing sleeve in a perspective transparent view.
FIG. 11 shows a stiffening element according to the exemplary embodiment in FIG. 10 in a perspective view.

FIG. 10 shows an exemplary embodiment of the electrode fixing sleeve 1 according to the present invention schematically in a transparent view. The same reference signs are used for elements that correspond in terms of function and/or design to the elements of the exemplary embodiments in the prior figures. For the sake of brevity, only the differences from the prior exemplary embodiments will be discussed.

In the exemplary embodiment in FIG. 10 too, the stiffening element 10 is cylindrical. The cylindrical stiffening element 10 of the exemplary embodiment in FIG. 10 does not require a clamping wedge, however. Rather, a receiving opening for a clamping element 41, which can exert a fastening force onto the electrode against the radial direction R, extends in the radial direction R.

Further details concerning the cylindrical stiffening element 10 can be better seen in FIG. 11, which merely illustrates the cylindrical stiffening element 10 and the clamping element 41 schematically in a perspective view.

The clamping element 41 can be formed as a screw, which can be inserted into the receiving opening provided in FIG. 11 with reference sign 42, against the radial direction R.

With direct contact between the clamping element 41 and the electrode, there is a risk of mechanical overload and subsequent damage to the electrode. In order to avoid such an overload of the electrode, the stiffening element 10 has at least one inner partial shell, which can be displaced by the clamping element 41 against the radial direction R toward the longitudinal axis L'. The inner partial shell 43 uniformly distributes fastening forces applied by the clamping element 41 over at least one side of the electrode.

The stiffening element 10 may have at least one further inner partial shell 44, which is arranged opposite the inner partial shell 43 transverse to the longitudinal direction L, with the result that the receiving tube 11 extends through the inner partial shells 43, 44, which border the receiving volume for the electrode, said receiving volume being defined by the receiving tube 11.

The inner partial shells 33, 34 can be fastened to a holding tube 45, which runs parallel to the radial direction R and which holds the inner partial shells 33, 34 in an open sate when the clamping element 41 is not inserted into the receiving opening 42. The clamping element 41 may press either directly onto the inner partial shell 43 or onto the holding tube 45 in order to press the partial shells 43, 44 together. Here, the holding tube 45 is preferably resiliently deformable, with the result that the holding shells 43, 44 are distanced from one another when the clamping element 41 is removed from the opening 42. The holding tube 45 is thus preferably arranged between the inner partial shells 43, 44 and an outer sleeve 46 of the stiffening element 10 in the radial direction R and secures the partial shells 43, 44 against displacements along the longitudinal direction and relative to the receiving opening 42.

Figure 12:
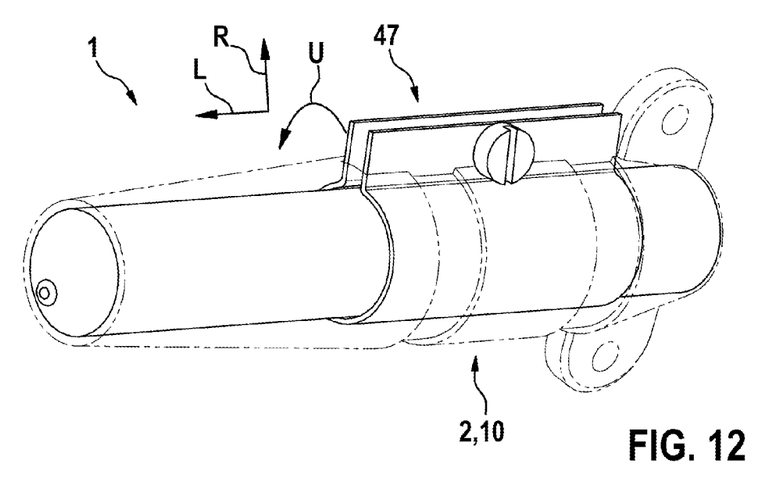
FIG. 12 shows a further exemplary embodiment of an electrode fixing sleeve in a perspective transparent view.

FIG. 12 shows a further exemplary embodiment of a stiffening element 10, comprising a clamping member, of the electrode fixing sleeve 1 schematically in a transparent perspective illustration. The same reference signs are used for elements that correspond in terms of function and/or design to the elements of the exemplary embodiments shown in the prior figures. For the sake of brevity, only the differences from the prior exemplary embodiments will be discussed.

FIG. 12 shows the electrode fixing sleeve 1 with a clamping member 47 for fastening the electrode, wherein the clamping member 47 partly forms the stiffening element 10 and is embedded in the wall material 8 of the electrode fixing sleeve 1.

Figure 13:
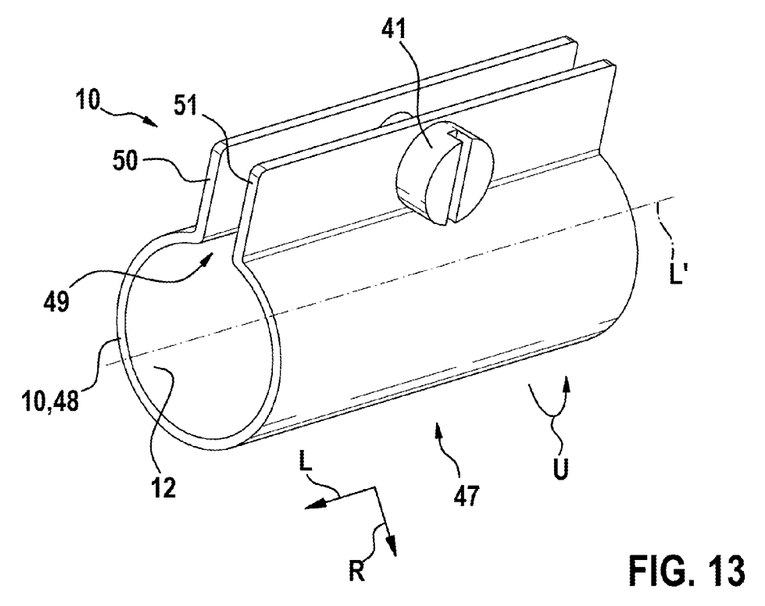
FIG. 13 shows a stiffening element according to the exemplary embodiment in FIG. 12 in a perspective view.

Further details concerning the clamping member 47 can be better seen in FIG. 13, since FIG. 13 shows only the clamping member 47 in a schematic perspective illustration.

The clamping member 47 is formed with a clamping portion 48, by means of which the electrode can be held in a force-locked manner in the electrode fixing sleeve 1 transversely to the longitudinal direction L. The clamping portion 48 simultaneously forms the stiffening element 10 since the clamping portion 48 uniformly distributes fastening forces acting on the clamping member 47 over the electrode. The stiffening element 10 may thus also be referred to rather generally as force distribution element for all exemplary embodiments.

The clamping portion 48 is substantially hollow-cylindrical and extends in the longitudinal direction L. The hollow-cylindrical clamping portion 48 has a gap 49 extending in the longitudinal direction L. Due to the gap 49, sides of the clamping portion 48 arranged opposite one another can be pressed toward one another.

To introduce the fastening force and to press together the clamping portion 48, the stiffening element 10 may comprise two force take-up portions 50, 51, which protrude parallel to one another in the radial direction R from ends of the clamping portion 48 that are arranged opposite one another in the circumferential direction U. The gap 49 extends between the ends of the clamping portion 48. The fastening force is introduced into the force take-up portions 50, 51. To this end, the force take-up portions 50, 51 may each have an opening, for example, wherein one of the openings is formed with an inner thread. If the clamping element 41, for example, a screw, is now inserted into the openings, the fastening element 41 can thus draw the take-up portions 50, 51 toward one another, whereby the sides of the clamping portion 48 arranged opposite one another are moved toward one another and the inner diameter of the receiving tube 11 is reduced.

At least the clamping portion 48 is embedded in the wall material 8 and, via its inner face 12, borders the receiving volume for the electrode, said receiving volume being defined by the receiving tube 11. The force take-up portions 50, 51 preferably protrude out from the wall material 8 from the longitudinal axis L' in order to be better accessible.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An electrode fixing sleeve for fixing an electrode to a tissue portion of a patient, comprising:
   a fastening portion for fastening the electrode fixing sleeve to the electrode, wherein the electrode fixing sleeve forms a receiving tube for the electrode, said receiving tube extending through the fastening portion in the longitudinal direction of said sleeve, wherein the fastening portion is compressible against a radial direction running perpendicularly to the longitudinal direction, and wherein the fastening portion has a greater rigidity than an adjacent portion of the electrode fixing sleeve,
   wherein the electrode fixing sleeve comprises a stiffening element which is arranged in the fastening portion and has a greater rigidity than a wall material of the electrode fixing sleeve, wherein the stiffening element is an integral component of the electrode fixing sleeve,
   wherein the stiffening element is deformable against the radial direction, and
   wherein deformation of the fixing sleeve against the radial direction causes a uniform reduction of an inner diameter of the stiffening element in the longitudinal direction.

2. The electrode fixing sleeve as claimed in claim 1, wherein the stiffening element is sunk into the wall material.

3. The electrode fixing sleeve as claimed in claim 1, wherein the stiffening element borders a receiving volume for the electrode, said receiving volume being defined by the receiving tube.

4. The electrode fixing sleeve as claimed in claim 1, wherein an inner face of the stiffening element is in line with an inner face of the fastening portion.

5. The electrode fixing sleeve as claimed in claim 1, wherein the stiffening element is formed as a hollow coil.

6. The electrode fixing sleeve as claimed in claim 5, wherein the hollow coil comprises a wound stiffening sheet, of which the faces running parallel to the longitudinal direction are larger than its faces running transversely to the longitudinal direction.

7. The electrode fixing sleeve as claimed in claim 6, wherein a distance, measured parallel to the longitudinal direction, between adjacent turns of the hollow coil is smaller than a width of the stiffening sheet measured parallel to the longitudinal direction.

8. The electrode fixing sleeve as claimed in claim 5, wherein the hollow coil has at least one turn.

9. The electrode fixing sleeve as claimed in claim 5, wherein the hollow coil has a whole number of turns.

10. A method for producing an electrode fixing sleeve for fixing an electrode to a tissue portion of a patient, comprising a fastening portion for fastening the electrode fixing sleeve to the electrode, wherein the electrode fixing sleeve comprising a receiving tube for the electrode, said receiving tube extending through the fastening portion in the longitudinal direction of said sleeve, and wherein the fastening portion is compressible against a radial direction running perpendicularly to the longitudinal direction, wherein the fastening portion is formed with a greater rigidity than an adjacent portion of the electrode fixing sleeve, wherein the electrode fixing sleeve comprises a stiffening element which is arranged in the fastening portion and has a greater rigidity than a wall material of the electrode fixing sleeve, wherein the stiffening element is an integral component of the electrode fixing sleeve, wherein the stiffening element is deformable against the radial direction, and wherein deformation of the fixing sleeve against the radial direction causes a uniform reduction of an inner diameter of the stiffening element in the longitudinal direction.

11. The method as claimed in claim 10, wherein a stiffening element is integrated into the fastening portion.

12. The method as claimed in claim 11, wherein the stiffening element is embedded in a wall material of the fastening portion.

13. The method as claimed in claim 11, wherein the wall material is cast around the stiffening element at least in portions.

* * * * *